(12) United States Patent
Neu et al.

(10) Patent No.: US 10,478,116 B2
(45) Date of Patent: Nov. 19, 2019

(54) METHODS AND SYSTEMS FOR FEEDING READINESS DIAGNOSIS

(71) Applicant: University of Florida Research Foundation, Inc., Gainesville, FL (US)

(72) Inventors: Josef Neu, Gainesville, FL (US); Sungho Oh, Daegu (KR); Jui-Hong Chien, Baltimore, MD (US); Eric Ortigoza, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 15/114,957

(22) PCT Filed: Jan. 30, 2015

(86) PCT No.: PCT/US2015/013984
§ 371 (c)(1),
(2) Date: Jul. 28, 2016

(87) PCT Pub. No.: WO2015/117035
PCT Pub. Date: Aug. 6, 2015

(65) Prior Publication Data
US 2016/0338634 A1    Nov. 24, 2016

Related U.S. Application Data

(60) Provisional application No. 61/933,562, filed on Jan. 30, 2014.

(51) Int. Cl.
*A61B 5/04*     (2006.01)
*A61B 5/00*     (2006.01)
(Continued)

(52) U.S. Cl.
CPC .......... *A61B 5/4238* (2013.01); *A61B 5/0075* (2013.01); *A61B 5/04* (2013.01);
(Continued)

(58) Field of Classification Search
CPC ..... A61B 5/4238; A61B 5/7275; A61B 7/008; A61B 5/04; A61B 5/14542; A61B 5/684;
(Continued)

(56) References Cited

U.S. PATENT DOCUMENTS

2003/0153847 A1   8/2003   Sandler et al.
2008/0306355 A1   12/2008  Walker
(Continued)

FOREIGN PATENT DOCUMENTS

WO    2012057406    5/2012

OTHER PUBLICATIONS

Brion, D., et al, Splanchnic tissue oxygenation, but not brain tissue oxygenation, increases after feeds in stable preterm neonates tolerating full bolus orogastric feeding, "J Perinatol", vol. 29 pp. 213-8 (2009).
(Continued)

*Primary Examiner* — Rex R Holmes
(74) *Attorney, Agent, or Firm* — Timothy H. Van Dyke; Beusse, Wolter, Sank & Maire PLLC

(57) ABSTRACT

An aspect of the invention described herein includes a method for a digestion diagnosis of a subject. The method includes obtaining electrogastrogram (EGG), bowel sound and NIRS signals from one or more sensors positioned about an abdominal region of a subject, removing artifacts from the signals to obtain conditioned signal data, and determining a digestion condition or feeding readiness of the subject based at least in part on the conditioned signal data.

19 Claims, 9 Drawing Sheets

(51) Int. Cl.
  A61B 5/0488 (2006.01)
  A61B 5/145 (2006.01)
  A61B 7/00 (2006.01)
  A61B 5/0476 (2006.01)

(52) U.S. Cl.
  CPC ...... *A61B 5/04884* (2013.01); *A61B 5/14542* (2013.01); *A61B 5/42* (2013.01); *A61B 5/684* (2013.01); *A61B 5/7207* (2013.01); *A61B 5/7221* (2013.01); *A61B 5/7264* (2013.01); *A61B 5/7275* (2013.01); *A61B 5/7282* (2013.01); *A61B 5/742* (2013.01); *A61B 7/008* (2013.01); *A61B 5/0476* (2013.01); *A61B 2503/045* (2013.01)

(58) Field of Classification Search
  CPC ..... A61B 5/7207; A61B 5/7264; A61B 5/742; A61B 5/7282; A61B 5/04884; A61B 5/0075; A61B 5/7221; A61B 5/42; A61B 5/047
  See application file for complete search history.

(56) References Cited

U.S. PATENT DOCUMENTS

| | | | |
|---|---|---|---|
| 2013/0046150 A1* | 2/2013 | Devanaboyina | A61B 5/0024 600/301 |
| 2013/0231577 A1 | 9/2013 | Leiderman | |

OTHER PUBLICATIONS

Chang Fy, Electrogastrography: basic knowledge, recording, processing and its clinical applications, "J Gastroenterol Hepatol" (2005) vol. 20, pp. 502-16.
Chen J. A computerized data analysis system for electrogastrogram, "Computers in Biol. and Med.", (1992), vol. 22, 9 pages.
Chen JD, et al., Detection of gastric slow wave propagation from the cutaneous electrogastrogram., "Am J Physiol", vol. 277, pp. G424-30 (1999).
Chen JD, et al., Patterns of gastric myoelectrical activity in human subjects of different ages, "Am J Physiol" (1997) vol. 272, pp. G1022-7.
Chen JD, et al., Serosal and cutaneous recordings of gastric myoelectrical activity in patients with gastroparesis, "Am J Physiol" (1994) vol. 266, pp. G90-8.
Craine BL, et al., Computerized auscultation applied to irritable bowel syndrome, "Dig Dis Sci" (1999) vol. 44, pp. 1887-92.
Devanarayana NM, et aL, Gastric myoelectrical and motor abnormalities in children and adolescents with functional recurrent abdominal pain, "J Gastroenterol Hepatol", (2008) vol. 23, pp.1672-7.
Farghaly, SA., Current diagnosis and management of ovarian cysts, "Clinical and Experimental Obstertrics & Gynecology", vol. 41, Issue 6, 144 pages (2014).
Fortune PM, et al., Cerebro-splanchnic oxygenation ratio (CSOR) using near infrared spectroscopy may be able to predict splanchnic ischaemia in neonates, "Intensive Care Med", (2001) vol. 27, pp. 1401-7.
Indrio F, et al., Effects of probiotic and prebiotic on gastrointestinal motility in newborns, "J. of physiol. and pharm." (2009) vol. 60, 7 pages.
Indrio F, et al., Prebiotics improve gastric motility and gastric electrical activity in preterm newborns, "J Pediatr Gastroenterol Nutr"(2009) vol. 49, pp 258-61.
Indrio F, et al., The effects of probiotics on feeding tolerance, bowel habits, and gastrointestinal motility in preterm newborns, "J. Pediatrics" (2008) vol. 152, 6 Pages.
Liang J, et al., Development of gastric slow waves in preterm infants measured by electrogastrography, "Am J Physiol" (1998) vol. 274, pp. G503-8.
Liatsos C, et al., Bowel sounds analysis: a novel noninvasive method for diagnosis of small-vol. ascites, "Dig Dis Sci" (2003) vol. 48, pp. 1630-6.
Lin X., Chen JZ, Abnormal gastric slow waves in patients with functional dyspepsia assessed by multichannel electrogastrography, "Am. J. Physiol. Gastrointest Liver Physiol." (2001) vol. 280, pp. G1370-1375.
Lin Z, et al., Postprandial response of gastric slow waves: correlation of serosal recordings with the electrogastrogram, "Dig Dis Sci", (2000) vol. 45, pp. 645-51.
McNeill S, et al, Normal cerebral, renal and abdominal regional oxygen saturations using near-infrared spectroscopy in preterm infants, "J Perinatol" (2010) vol. 31, pp. 51-7.
Parkman HP, et al., Electrogastrography: a document prepared by the gastric section of the American Motility Society Clinical GI Motility Testing Task Force, "Neurogastroenterol Motil" (2003) vol. 15, pp. 89-102.
Patterson M, et al., A longitudinal study of electrogastrography in normal neonates, "J. Pediatric Surg." (2000) vol.35, pp. 59-61.
Riezzo G, et al., Gastric electrical activity and gastric emptying in preterm newborns fed standard and hydrolysate formulas, "J Pediatr Gastroenterol Nutr" (2001), vol. 33, pp. 290-5.
Riezzo G, et al., Gastric electrical activity in normal neonates during the first year of life: effect of feeding with breast milk and formula, "J. Gastroenterol", (2003), vol. 38, pp. 836-843.
Rossi Z, et al., Electrogastrography, "Eur Rev Med Pharmacol Sci", vol. 9, pp. 29-35 (2005).
Safder S, et al., Gastric electrical activity becomes abnormal in the upright position in patients with postural tachycardia syndrome, "J Pediatr Gastroenterol Nutr", vol. 51, pp. 314-318 (2010).
Stapleton GE, et al., Mesenteric oxygen desaturation in an infant with congenital heart disease and necrotizing enterocolitis. "Texas Heart Institute J." (2007) vol. 34, 3 pages.
Tomomasa T, et al., Analysis of gastrointestinal sounds in infants with pyloric stenosis before and after pyloromyotomy, "Pediatrics" (1999) vol. 104, 6 pages.
Tomomasa T, et al., Gastrointestinal sounds and migrating motor complex in fasted humans, "Am J Gatroenterol"(1999) vol. 94, pp 374-81.
Yamaguchi K, et al., Evaluation of gastrointestinal motility by computerized analysis of abdominal auscultation findings, "J Gastroenterol Hepatol" (2006) vol. 21, pp. 510-4.
Yin J, Chen JD, Electrogastrography: methodology, validation and applications, "J Neurogastroenterol Motil", vol. 19, pp. 5-17 (2013).
Zhang J, et al, Development of gastric slow waves and effects of feeding in pre-term and full-term infants, "Neurogastroenterol Motil." (2006) vol. 18, pp. 284-291.

* cited by examiner

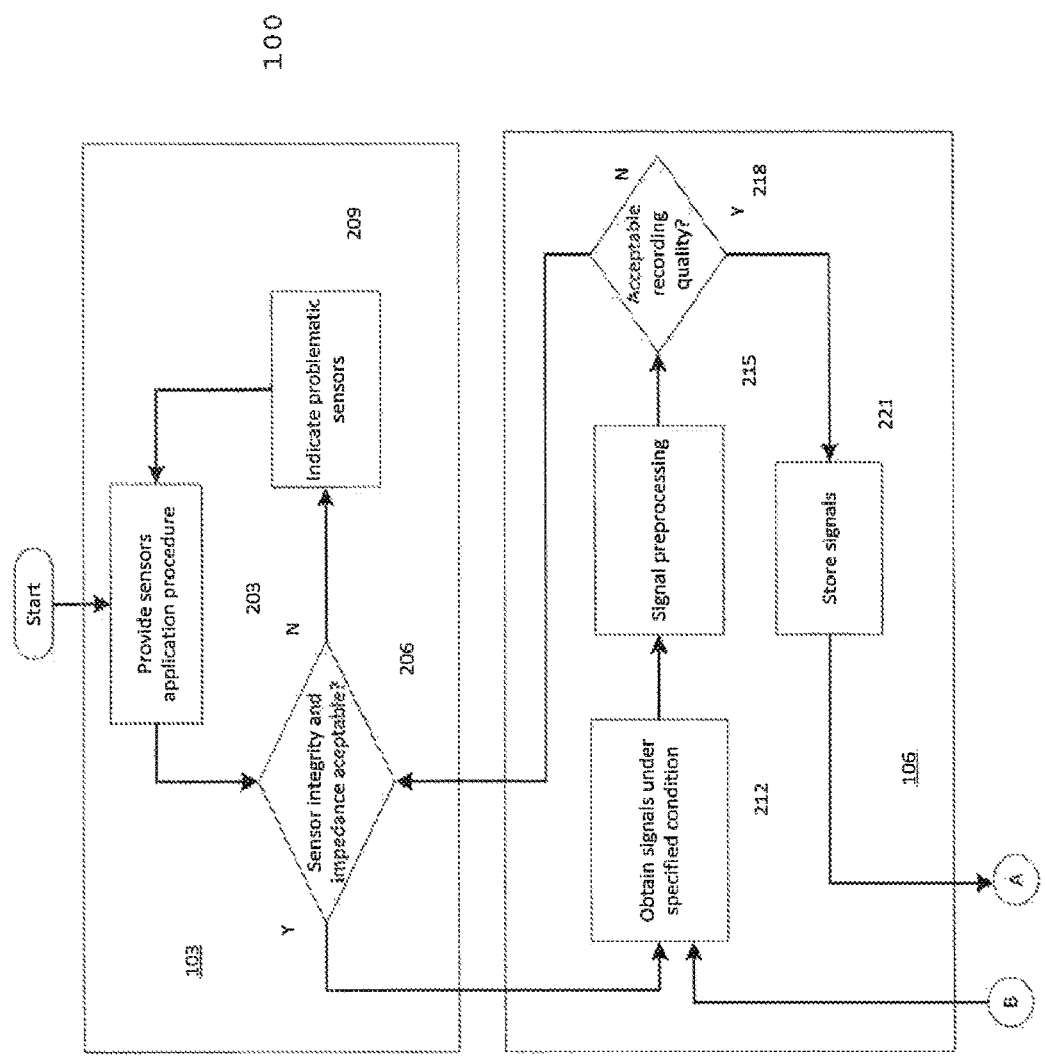

_US 10,478,116 B2_

METHODS AND SYSTEMS FOR FEEDING READINESS DIAGNOSIS

BACKGROUND

Feeding intolerance is very common especially in the very low birth-weight infants (VLBW) infants. This is a major concern for neonatologists, and controversy exists regarding how fast to advance enteral feedings. Current decisions to feed the premature infants are based on indicators such as gastric residuals, abdominal circumference and clinical appearance. These are highly subjective and provide poor evidence about feeding readiness. In fact, gastric residual measurements may have some unwanted side effects such as gastric mucosal disruption and removal of active enzymes and gastric acid. Reliance on such subjective clinical judgment rather than objective criteria often results in overly aggressive feeding the infants with high risk of developing necrotizing enterocolitis (NEC), or underfeeding that can lead to growth failure, atrophy of the bowel, increased inflammatory responses, and an increased likelihood for the development of sepsis.

An important task is to clarify whether the neonatal gastrointestinal (GI) tract has matured adequately for accepting feeding advancements. Objective and scientific investigations are necessary to clarify if the signs of feeding intolerance are predictive of NEC or due to normal maturation patterns. For the infants who have had surgery for bowel disease such as gastroschisis and necrotizing enterocolitis (NEC), metabolic demands are increased due to overlapping requirements for growth and recovery. A means for determining enteral feeding readiness is crucial for these infants.

Premature feeding attempts may exacerbate feeding intolerance, while lack of enteral feedings will prolong intravenous nutrition and its associated complications. Current decisions on when to introduce feedings in these infants are based on clinical criteria such as stool passage and presence of bowel sounds supported by conventional auscultation technique. Many infants (i.e. those with gastroschisis) have never been fed and have little stool to pass. Presence or absence of bowel sounds is not very reliable for the prediction of feeding readiness in these infants. Prediction may be improved by using alternative non-invasive investigations of bowel motility or more rigorous objective investigation of bowel sounds. The ability to accurately discern the babies who can be safely fed and have their enteral feedings increased versus the ones who cannot would be a critical advance in neonatal intensive care. Methods currently used in the neonatal GI evaluation include plain radiography, which is readily applicable and valuable in detecting NEC, bowel performance, and bowel obstruction. However, the information that can be obtained regarding gut motility and feeding readiness using this method is very limited. While contrast studies can provide some functional information about gastric emptying or intestinal transit that is derived from anatomic delineation, radiography is limited in that it is a qualitative assessment method and produces planar and snapshot images of a single point in time. Scintigraphy, which is not a widely used method in infants, can also be used for motility research. A gamma camera is used to image radionuclide tracers in GI transit studies. It is limited, however, by poor image resolution, interpretational difficulty for overlapping intestine, and practical difficulty of moving patients to the testing site. Radiation exposure is a critical drawback for both radiography and scintigraphy.

Therefore, current technologies are limited in validation, practical application and patient safety. Therefore, the evaluation of feeding readiness in premature infants using these methods is less than satisfactory, and continuing efforts for developing better assessment modalities are needed.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1 is a block diagram illustrating an example of a system for evaluating a feeding condition of a neonate in accordance with various embodiments of the present disclosure.

FIGS. 2A and 2B are flowcharts illustrating an example of functionality of the system of FIG. 1 in accordance with various embodiments of the present disclosure.

DETAILED DESCRIPTION

Figure 2B:
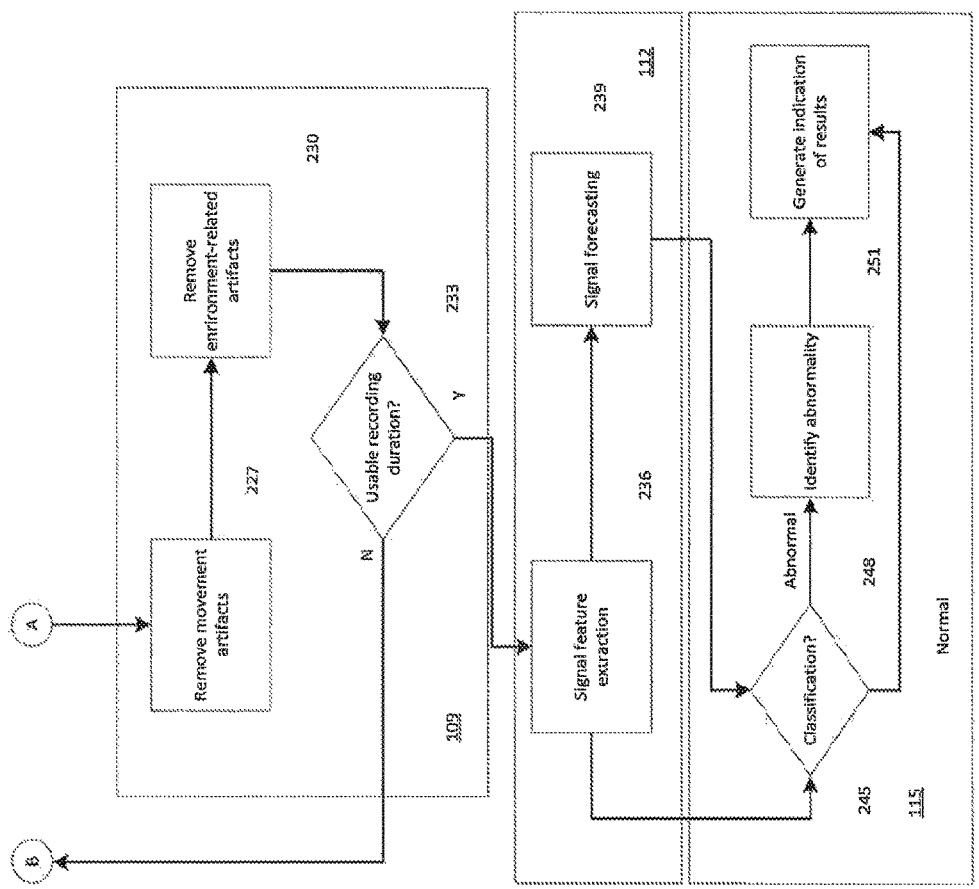

Disclosed herein are various embodiments of methods and systems related to diagnosis of feeding intolerance conditions or the diagnosis of normal physiological gastrointestinal states (e.g. assessment of the digestion function or monitoring level of feeding readiness). For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

It is to be noted that the terms "first," "second," and the like as used herein do not denote any order, quantity, or importance, but rather are used to distinguish one element from another. The terms "a" and "an" do not denote a limitation of quantity, but rather denote the presence of at least one of the referenced item.

The terminology used herein is for the purpose of describing particular embodiments only and is not intended to be limiting. As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising."

The term "processor" or "processing module" may include a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions. The processing module may have operationally coupled thereto, or integrated therewith, a memory component. The memory component may be a single memory component or a plurality of memory components. Such a memory component may be a read-only memory (ROM), random access memory (RAM), volatile memory, non-volatile memory, static memory, dynamic memory, flash memory, an erasable programmable read-only memory (EPROM or Flash memory), an optical fiber, and a portable compact disc read-only memory (CD-ROM), a CD ROM, a DVD (digital video disk), and/or any other electronic device that stores digital information.

A "computer" or "computer unit", as used herein, is intended to include at least one device that comprises at least one processing module (e.g. processor). In a typical embodiment, a computer unit includes at least one processing module, a memory component, and circuitry connecting the at least one processing module and said memory component in a housing. Optionally, the computer unit includes a computer readable medium and circuitry connecting the processing module and computer readable medium. A computer unit is also intended to include two or more computer units hardwired together.

The computer-usable or computer-readable medium may be or include, for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM), a CD ROM, a DVD (digital video disk), or other electronic storage medium.

The term "communicatingly connected" means that one-way or two-way conveyance or communication of information. Typically, information is electronic information that is conveyed through a wired connection or transmitted wirelessly. Two different computer units may be communicatingly connected, a computer unit and a peripheral device (e.g. printer) and/or components of a computer unit may be communicatingly connected (e.g., a processing module may be communicatingly connected to memory component. Communicatingly connected may also include conveyance of information via a network (e.g. internet) to a remote computer. Conveyance of information may include transference of an electronic record, such as transfer of an email or email attachment or transfer of a file via a network. Conveyance of information may include transference of a facsimile file to a facsimile computer unit.

Computer program code for carrying out operations of certain embodiments of the present invention may be written in an object oriented and/or conventional procedural programming languages including, but not limited to, Java, Smalltalk, Perl, Python, Ruby, Lisp, PHP, "C", FORTRAN, or C++. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

Certain embodiments of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer-readable program code modules. These program code modules may be provided to a processing module of a general purpose computer, special purpose computer, embedded processor or other programmable data processing apparatus to produce a machine, such that the program code modules, which execute via the processing module of the computer or other programmable data processing apparatus, create means for implementing the functions specified in the flowchart and/or block diagram block or blocks.

These computer program code modules may also be stored in a computer-readable memory that can direct a computer or other programmable data processing apparatus to function in a particular manner, such that the program code modules stored in the computer-readable memory produce an article of manufacture.

The computer program code modules may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart and/or block diagram block or blocks.

It should be noted that the terms "may," "might," "can," and "could" are non-limiting terms used to indicate that the described term may include alternatives and optional features.

It should be noted that, unless otherwise specified, the term "or" is used in its nonexclusive form (e.g. "A or B" includes A, B, A and B, or any combination thereof, but it would not have to include all of these possibilities). It should be noted that, unless otherwise specified, "and/or" is used similarly (e.g. "A and/or B" includes A or B or A and B, or any combination thereof, but it would not have to include all of these possibilities). It should be noted that, unless otherwise specified, the term "includes" means "comprises" (e.g. a device that includes or comprises A and B contains A and B but optionally may contain C or additional components other than A and B). It should be noted that, unless otherwise specified, the singular forms "a," "an," and "the" refer to one or more than one, unless the context clearly dictates otherwise.

It has been discovered that there is currently no objective method available on the bed-side that evaluates feeding readiness and digestive condition, particularly for premature and/or VLBW infants. Therefore, the inventors have discovered for non-invasive and safe technological evaluation herein, a method of neonatal gastrointestinal motility monitoring. Measurements can be made simultaneously using near infrared spectroscopy (NIRS), electrogastrography (EGG), and bowel sounds monitors, or in other embodiments, by a combination of at least two of methods. Thoughtful synergistic integration of these methods is likely to serve as a useful tool for the clinicians to safely determine digestive conditions and feeding readiness in these vulnerable infants.

Electrogastrography is a technology for measuring the voltage, waveform and frequency of the electrical activity from stomach wall muscles. Electrogastrogram (EGG) electrodes can record gastric or intestinal muscle activity at abdominal skin. A EGG is the least invasive methodology, making it widely used in medicine and research, for example, to aid in the diagnosis of digestion disorders such as feeding intolerance, recurrent nausea, vomiting, stomach trauma, digestion system infections, stomach tumors, degenerative disorders of the stomach, assessment of digestion disorders, and monitoring of stomach function during feeding through the recording gastric muscle electrical activity and interpretation of the spatial-temporal patterns of that activity. By analyzing the EGG data over a period of time, digestion states can be identified and persistent disturbances of stomach function can be detected.

Quantitative analysis of bowel sounds may help provide objective interpretation of the acoustical activities of the intestine associated with motility. Near Infrared Spectroscopy (NIRS) can be used to measure regional tissue oxygenation for a continuous period of time. The inventors have discovered that analyzing EGG, bowel sound, and NIRS signals together reveals the pattern and dynamics of the digestion state as the premature neonate goes through various physiological and development states. Additionally, with the inventive methods and techniques developed herein, a critical destruction of digestion function, such as necrotizing enterocolitis can be detected.

Necrotizing enterocolitis (NEC) is the death of intestinal tissue which most often affects premature or sick babies. This condition occurs when the lining of the intestinal wall dies and the tissue falls off. NEC is a significant cause of destruction of digestive function in premature newborns.

Provided in embodiments herein are systems and methods for reliably obtaining and evaluating recorded GI signals in real time by algorithms and providing an indication of the digestion condition of a subject. The term "digestion condition" as used herein may include a normal (healthy) or abnormal condition of the digestion system of a subject. Furthermore, the digestion condition may include the feeding readiness or non-readiness of a subject.

As used herein, the terms "subject" and "patient" are used interchangeably. As used herein, the term "subject" refers to an animal, preferably a mammal such as a non-primate (e.g., cows, pigs, horses, cats, dogs, rats etc.) and a primate (e.g., monkey and human), and most preferably a human, in most cases a very low birth-weight infant (VLBW) or a neonate.

The acquired data may be evaluated in real time and/or may be stored for subsequent evaluation. The system allows EGG, bowel sound and NIRS data to be recorded and evaluated in cases when no technical personnel are readily available, allowing its use as a diagnostic screening or monitoring tool to assist care-givers when trained physicians are unavailable. The original data may also be stored for subsequent visual analysis and interpretation and/or may be transmitted to remote sites for review and interpretation by experts.

EGG, bowel sound and NIRS data can be recorded with small, portable, inexpensive instruments that do not require special shielded facilities or the subject remaining motionless for long periods of time. Thus, for example, an EGG can be utilized in noisy point-of-care environments, such as emergency rooms (ERs) and neonate intensive care units (NICUs) and with subjects who may be uncooperative. Portable recording units can also be utilized in emergency vehicles and in the field. The system described herein in one embodiment may be used for, but is not limited to, digestion assessment such as, e.g., regions of transient disturbance, ischemic events, and chronic inflammation. Acute and subacute inflammation include such disorders as those due to traumatic stomach injuries, toxic response (e.g. drug or alcohol toxicity), metabolic disorders (e.g. hypoglycemia, hyperglycemia, ketoacidosis, renal failure, hepatic failure, hypoxia, hypercapnea), acute or subacute infections of the digestion system, transient ischemic attacks, and autoimmune disorders affecting the digestion system. It may also be used for detecting mild disturbances of digestion function including, e.g., feeding intolerance, which may be difficult to detect reliabley and accurately using standard clinical examinations or test procedures. Information obtained through the system 100 may be used to refine the differential diagnosis, formulate further workup (e.g. imaging procedures) and treatment, and for purposes of triage and referral to appropriate facilities and specialists.

Thus in one embodiment, a method for a digestion diagnosis of a subject is provided. The method includes obtaining electrogastrogram (EGG), bowel sound and NIRS signals from one or more sensors positioned about an abdominal region of a subject, removing artifacts from the signals to obtain conditioned signal data, and determining a digestion condition or feeding readiness of the subject based at least in part on the conditioned signal data.

In a further embodiment, the method may include determining gastrointestinal (GI) signal features from the conditioned GI signal data, wherein the digestion condition is base at least in part upon the GI signal features.

In one particular embodiment, the artifacts include movement artifacts, recording environment-related artifacts, and sensor-related artifacts, or a combination thereof. In another embodiment, determining the digestion condition of the subject comprises identifying an abnormal digestion condition, determining a location of an abnormal condition, and determining a severity of an abnormal condition, or a combination thereof.

In another embodiment, a system for cerebral diagnosis is provided. The system includes a signal recording module configured to acquire GI signals from one or more sensors positioned about an abdominal region of a subject, a signal conditioning module configured to condition GI signal data from the one or more GI signals, a signal analysis module configured to determine at least one feature of a GI signal based at least in part on the conditioned GI signal data, and a condition classification module configured to determine a digestion condition of the subject based at least in part on the at least one determined feature.

In a further embodiment, the system includes a sensor application module configured to verify a recording condition of the one or more sensors based upon predefined sensor criteria. In yet a further embodiment, the signal conditioning module is configured to remove, from the GI signal data, artifacts associated with movement of the subject.

In another embodiment, the signal analysis module is configured to generate a cerebral network model based at least in part upon the conditioned GI signal data. In a further embodiment, the condition classification module is configured to identify a location and a severity of an abnormal digestion condition. In some instances, the abnormal digestion condition includes bowel ischemia or NEC. In another embodiment, a method for digestion diagnosis is provided. The method includes positioning one or more electrogastrogram (EGG) electrodes, bowel sound stethoscopes and/or near-inferred spectroscopy (NIRS) sensors about an abdominal region of a subject. The method further includes determining with a processor a recording condition for each of the one or more sensors based upon predefined sensor criteria, wherein when an acceptable recording condition is identified, one or more signals are obtained from the one or more sensors, and wherein when an unacceptable recording condition is identified, an indication of the sensor corresponding to the unacceptable recording condition is provided. In another embodiment, the method further includes wherein following an indication of the sensor corresponding to the unacceptable recording condition, a communication to a user for correction of the unacceptable recording condition is provided.

In yet another embodiment, the method further includes amplification and filtering of the one or more obtained GI signals. In still a further embodiment, the method includes sampling the one or more obtained GI signals to obtain digital CI data.

In another embodiment the digital GI data is stored in memory. In yet another embodiment a backup of the digital GI data is provided by a computer unit or a server, or a combination thereof.

Turning to the drawings, FIGS. 1 and 2 provide a block diagram and a flow diagram, respectively, illustrating an embodiment of a system 100 for evaluating a digestion condition of a subject. Reference to "nodes" herein refers to an operation step of a module of the system. In the embodiment of FIG. 1, the system 100 includes an sensor application module 103, a GI signal recording module 106, a signal conditioning module 109, a signal analysis module 112, and a condition classification module 115. The system 100 may contain an interactive display which may provide, e.g., step-by-step instructions on electrode placement, establishing connections, preparing the subject and initiating the recording, etc. The system 100 allows for rapid acquisition and analysis of signals, measurement of the temporal characteristics of the EGG, bowel sound and NIRS signal, analysis of local, regional, and diffuse signal characteristics, determination of whether or not these characteristics are normal or abnormal, and classification of abnormal recordings to reveal whether the abnormalities are acute or persistent. The results may be displayed as in a text, verbal, and/or graphical format that may be available for immediate use by emergency room personnel, intensive care personnel, and emergency medical technicians.

Referring to FIG. 2, shown is a flowchart illustrating various functions that may be implemented by modules of the system 100. After operation of the system has been initiated (e.g., by turning on the device), an electrode application procedure may be provided node 203 by the electrode application module 103 for rendering on the system display. The EGG, bowel sound and NIRS signals provides direct information about stomach functions through analysis of ongoing stomach activity. Depending on the location and the type of the electrodes, signals can reveal different levels of digestion activity. Numerous sensors may be applied to a subject to obtain EGG data containing information from stomach and intestine activity in both temporal and spatial domains. The sensors can include individual electrodes and/or an array of electrodes that are positioned on the abdominal skin. Distinct landmarks are often used, to infer the location of the subject's stomach. These landmarks are first identified, examples of such landmarks known in the art the umbilicus or right mid-clavicle. Sensors are thereafter placed at specific relative distances along the landmarks. The recording integrity and impedance of the sensors are verified in node 206 to determine if there is a problem with the placement and/or operation of the sensors. If there is a problem, the problematic sensor may be indicated in node 209 on the system display and the appropriate application procedure(s) may be provided in node 203. Guiding the operator through simple set-up and operating procedures to obtain a technically adequate recording reduces evaluation errors.

If the sensor integrity and impedance is acceptable in node 206, then EGG, bowel sound and NIRS signals are obtained under specified conditions in node 212 by the signal recording module 106. For example, EGG may be obtained, e.g., when the subject is crying and/or moving, at rest or during external stimulation (e.g. visual, somatic or auditory stimulation) or under other specified conditions. Instructions may be rendered for display on the system display to prompt the specified condition (or action) in the monitored subject. The acquired EGG, bowel sound and NIRS signals are then processed in node 215. For example, amplification and filtering may be applied to enhance the signal-to-noise ratio (SNR) of the signals. Analog signals from the sensors may also be digitized for communication and storage of the information. In node 218, acceptability of the recording quality of the data is confirmed. For example, all channels of the processed signal may be analyzed for the presence of excessive artifacts that may contaminate the data. Criteria for acceptable signal quality may be predefined to ensure acceptable sensor contact, electrode impedance, and minimal interference by common artifacts. Common artifacts filtered out of the signal may include noise in the neonatal intensive care unit, baby movement, crying, heart-rate, and breathing signals. If the signal quality is not acceptable, then the system can return to node 206 to recheck sensor integrity and electrode impedance. Common technical problems that degrade the recording (e.g., excess voluntary muscle artifacts) may also be determined in node 218. Instructions may be provided through the system display to guide the operator in methods to eliminate or attenuate those artifacts before repeating the acquisition of signals in node 212. Subsequent recorded data may be re-evaluated and the operator notified of persistent problems, at which time the operator may attempt to obtain further signals or may abort the procedure. If the data is acceptable, the digitized data can be stored in data storage or other memory devices in node 221. The stored data may be transmitted through a wireless or wired network connection (e.g., cellular, Bluetooth, Ethernet, etc.) for remote evaluation, analysis, and/or confirmation.

The acceptable data is further processed and/or filtered by the signal conditioning module 109 to remove common recording artifacts as illustrated in FIG. 2B. These artifacts are automatically detected, based upon, for example, their frequency, waveform, and spatial and temporal characteristics. For example, electromyogram (voluntary muscle movement) artifacts may be detected and removed in node 227, and electrode related artifacts such as, e.g., electromagnetic interference from nearby instruments may be detected and removed in node 230. Other artifacts such as, e.g., 60 Hz line signals and signals produced by mechanical ventilators and other instruments may also be detected and removed from the EGG data by the signal conditioning module 109. For example, epochs of data may be examined sequentially for the presence of an artifact. If a segment contains an excessive artifact, it may then be excluded from subsequent analysis. After the signal conditioning module 109 identifies and discards the artifact-contaminated segments, the remaining data is evaluated in node 233 to ensure that a useable signal of sufficient duration has been acquired and is available for analysis. An initial interpretation may be generated based upon a brief recording (e.g., 2 to 5 minutes). If the available data is not long enough for reliable analysis, the system 100 will inform the operator and return to node 212 to obtain additional data. If the available data is long enough for analysis or evaluation, the data is processed by the signal analysis module 112 to extract features in node 236.

The system 100 may also provide an option to continue recording to obtain routine EGG (typically around three hours of recording) or for continued monitoring for changes in stomach or intestine function, such as gastric trauma, focal ischemia, and changes in digestion states. In other implementations, the system 100 may be placed in a monitoring mode in which epochs of the signals are analyzed as they are acquired to detect transient abnormalities or state changes in the subject. In the monitoring mode, a continuous or intermittent analysis may be provided graphically and/or a summary report may be provided intermittently at specified intervals. For example, the interval between reports can be a default interval (e.g., every 10 minutes) or can be an interval that is selected by the operator.

The extracted features of the EGG, bowel sound and NIRS data from node 236 may be used to provide a quantitative description of the spatiotemporal characteristics of the signals, including local and regional characteristics. The extracted features may be, e.g., linear, non-linear, univariate, or bivariate statistics. The extracted features from node 236 may be provided as inputs for forecasting in node 239 and for classification of the digestion condition in node 245 of the condition classification module 115. For example, if the feature is univariate, such as entropy, each sensor will have a feature time series.

Classification of the digestion condition in node 245 may be based, at least in part, upon comparison of extracted features from nodes 236 and 242 by comparison with established norms to determine if they indicate a normal condition within normal limits or an abnormal condition.

If the digestion condition is determined to be abnormal, then the location of abnormal features (e.g. low oxygenation, or no muscle contraction) and/or the severity of the abnormality (e.g., mild, moderate, or severe) may be identified in node 248. For example, the condition may be identified as necrotizing enterocolitis. An indication of the classification results may then be generated in node 251 for rendering on the system display. A warning may be generated when an abnormal condition has been indicated.

A summary (or report) of findings may be provided in several forms which may be selected by the user. For example, a default condition may provide a report labeled as normal or indicating the determined abnormal category classification (e.g., mildly abnormal). Other graphical displays which provide maps of one or more individual signal property may also be viewed. The results of the classifications may also be stored in node 251 for later access or retrieval to further evaluation, interpretations, and validation.

Figure 3:
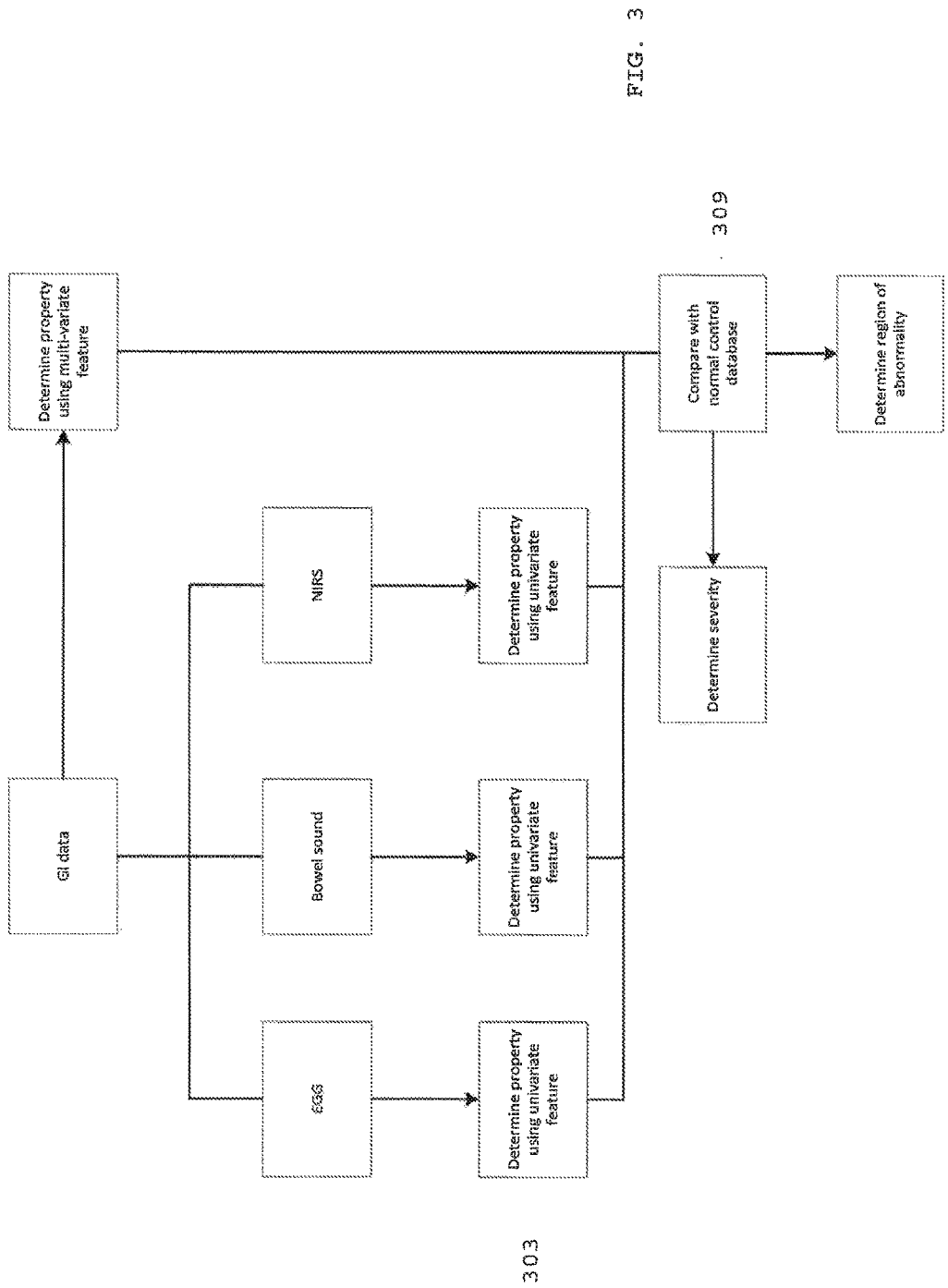
FIG. 3 is a flowchart illustrating examples of signals feature extraction, and classification of the flowchart of FIG. 2B in accordance with various embodiments of the present disclosure.

Referring to FIG. 3, shown is a flowchart illustrating examples of feature extraction and classification of the flowchart of FIG. 2B. In FIG. 3, EGG, bowel sound and NIRS data is received for signal feature extraction per node 236. Local properties may be determined from the data including the univariate feature. Kaiser-Teager energy and power in the signals may be computed for each sensor site.

Local energy and power properties may be determined for each channel for comparison to predetermined normative values for each channel. Abnormality of Teager energy and abnormalities for power would be expected to be either higher or lower than the normative values. Abnormalities in the Teager energy to Power ratio would be expected to be lower than norms. Norms may be derived from EGG recordings obtained from a normal test group, with appropriate age matching, or may be based upon baseline recordings obtained in the same subject (in which case, a change from baseline would be detected).

For each sensor channel, the following local property values may be computed in node 303:

Kaiser-Teager energy (KTE). KTE may be calculated for each electrode channel. This value can be obtained for the entire recorded frequency range as well as for each of the digestion muscle group signature frequency bands (stomach: 3 cycle/minute, duodenum: 12 cycle/minute, ileum: 8 cycle/minute, in some cases neonates may contract faster than adults). The value may be compared to normal values (node 309). If the values are outside of the normal range, the degree of abnormality (e.g., based on standard deviations (s.d.) from the mean) for each electrode channel can be determined. The location and degree of abnormality (1 s.d.$\geq$x<2 s.d., 2 s.d.$\leq$x<3 s.d, or x$\geq$3 s.d.) can be stored and used in the final evaluation and report.

Power. Standard power for the entire frequency range may be computed for each EGG electrode as well as bowel sound stethoscope and compared to normal values for each respective channel. If the values are outside of the normal range, the degree of abnormality (based on standard deviations from the mean) for each electrode channel can be determined. The location (left cerebral hemisphere, right cerebral hemisphere or bilateral) and degree of abnormality (1 s.d.≥x<2 s.d., 2 s.d.≤x<3 s.d, or x≥3 s.d.) can be stored and used in the final evaluation and report.

Relative ratios are generated for EGG and bowel sound for entire frequency range (in a typical embodiment). For EGG and bowel sound channel, the KTE to power ratio may be calculated for the entire recorded frequency range as well as for the standard EGG frequency bands is calculated for each channel and compared to normal values. If the values are outside of the normal range, the degree of abnormality (based on standard deviations from the mean) for each electrode channel can determined. The location (stomach, duodenum or ileum) and degree of abnormality (1 s.d.≥x<2 s.d., 2 s.d.≤x<3 s.d, or x≥3 s.d.) can be stored and used in the final evaluation and report.

The digestion condition can be classified in node 245 of FIG. 2 based upon comparison of values from nodes 309 of FIG. 3. After signals have been analyzed and results stored, the EGG data may be classified, based on the composite results from all, or a subset, of each individual analysis. If all of these analyses are within acceptable range of normal values, the recording may be classified as normal.

If there are abnormalities identified, the data will be classified as abnormal and assigned to one of several abnormal categories in node 248 of FIG. 2B. For example, the abnormal categories may be defined as follows: (1) NEC, (2) suspicious feeding intolerance, (3) mild digestion abnormality. Other digestion issues typically seen in neonates as known in the art may provide additional abnormal categories. As discussed above, the degree of abnormality may be based on standard deviations or other statistics from the mean values for each sensor channel. In some cases, a weighed combination of the standard deviations may be used to indicate the degree of abnormality. The results of the abnormality identification may be stored in a data store or memory and may be used to generate an indication for the operator of the system 100.

Figure 4:
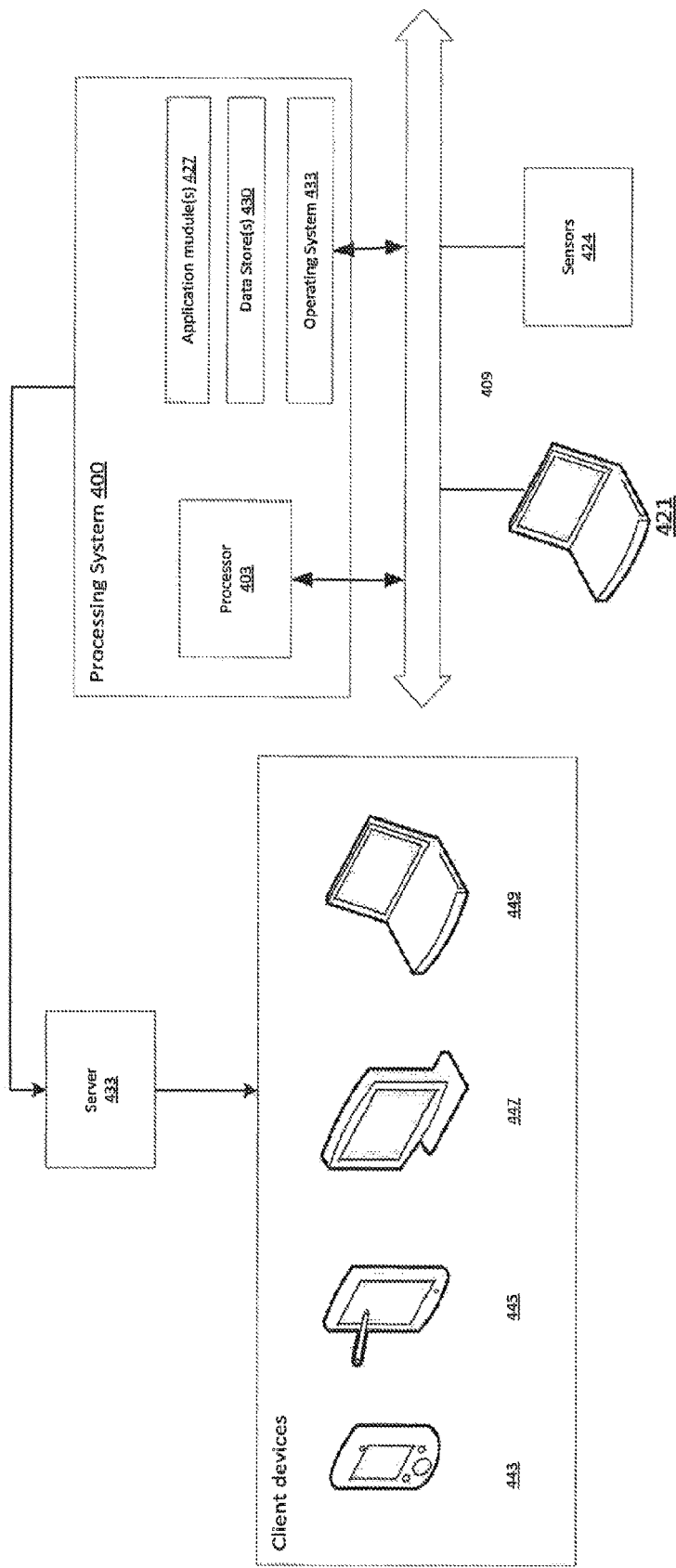
FIG. 4 is a graphical representation of an example of a processor system suitable for implementing the system of FIG. 1 in accordance with various embodiments of the present disclosure.

With reference to FIG. 4, shown is a schematic block diagram of a processor system 400 in accordance with various embodiments of the present disclosure. The processor system 400 includes at least one processor circuit, for example, having a processor 403 and a memory 406, both of which are coupled to a local interface 409. To this end, the processor system 400 may comprise, for example, at least one computer or like device. The local interface 409 may comprise, for example, a data bus with an accompanying address/control bus or other bus structure as can be appreciated. In addition, the processor system 400 includes operator interface devices such as, e.g., a display device 412, a keyboard 415, and/or a mouse 418. In some implementations, the operator interface device may be interactive display 421 (e.g., a touch screen) that provides various functionality for operator interaction with the processor system 400. Various sensors such as, e.g., EGG electrodes 424 may also interface with the processor system 400 to allow for acquisition of EGG signals from a subject. In some embodiments, the EGG electrodes 424 may be an array of electrodes configured to be positioned about the subject's head.

Stored in the memory 406 are both data and several components that are executable by the processor 403. In particular, stored in the memory 406 and executable by the processor 403 are various application modules 427 such as, e.g., an electrode application module 103, an EGG recording module 106, a signal conditioning module 109, a signal analysis module 112, and a condition classification module 115 of FIG. 1, and/or other applications. Also stored in the memory 406 may be a data store 430 and other data. In addition, an operating system 433 may be stored in the memory 406 and executable by the processor 403.

It is understood that there may be other applications that are stored in the memory 406 and are executable by the processor 403 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Delphi®, Flash®, or other programming languages.

A number of software components are stored in the memory 406 and are executable by the processor 403. In this respect, the term "executable" means a program file that is in a form that can ultimately be run by the processor 403. Examples of executable programs may be, for example, a compiled program that can be translated into machine code in a format that can be loaded into a random access portion of the memory 406 and run by the processor 403, source code that may be expressed in proper format such as object code that is capable of being loaded into a random access portion of the memory 406 and executed by the processor 403, or source code that may be interpreted by another executable program to generate instructions in a random access portion of the memory 406 to be executed by the processor 403, etc. An executable program may be stored in any portion or component of the memory 406 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 406 is defined herein as including both volatile and nonvolatile memory and data storage components. Volatile components are those that do not retain data values upon loss of power. Nonvolatile components are those that retain data upon a loss of power. Thus, the memory 406 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 403 may represent multiple processors 403 and the memory 406 may represent multiple memories 406 that operate in parallel processing circuits, respectively. In such a case, the local interface 409 may be an appropriate network that facilitates communication between any two of the multiple processors 403, between any processor 403 and any of the memories 406, or between any two of the memories 406, etc. The local interface 409 may comprise additional systems designed to coordinate this communication, including, for example, performing load balancing. The processor 403 may be of electrical or of some other available construction.

Although the sensor application module 103, the recording module 106, the signal conditioning module 109, the signal analysis module 112, the condition classification module 115, and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

Although the flowcharts of FIGS. 2A-2B and 3 show a specific order of execution, it is understood that the order of execution may differ from that which is depicted. For example, the order of execution of two or more blocks may be scrambled relative to the order shown. Also, two or more blocks shown in succession in FIGS. 2A-2B may be executed concurrently or with partial concurrence. Further, in some embodiments, one or more of the blocks shown in FIGS. 2A-2B may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including the sensor application module 103, the recording module 106, the signal conditioning module 109, the signal analysis module 112, the condition classification module 115, and/or application(s), that comprises software or code can be embodied in any non-transitory computer-readable medium for use by or in connection with an instruction execution system such as, for example, a processor 403 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Figure 5:
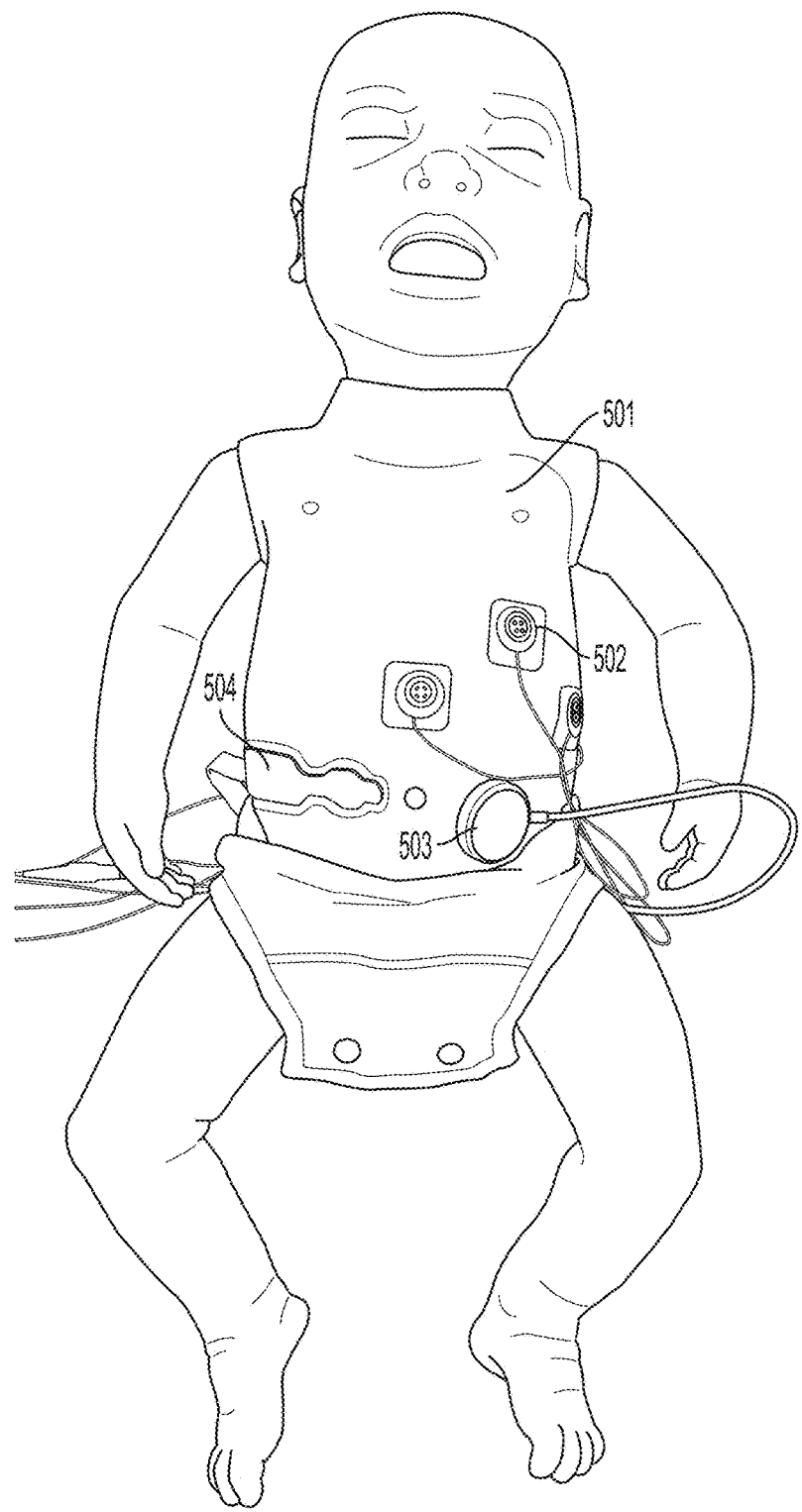
FIG. 5 shows a typical setup of sensors on a doll model.

Turning to FIG. 5, shown is a baby model 501 to illustrate placement of NIRS sensor (502), acoustic sensor (503) and EGG sensor (504).

EXAMPLES

Ref Nos in Parentheses

Background

Very low birth weight (VLBW) premature neonates who are able to be fed enterally have decreased morbidity and mortality.(1) Enteral feeding significantly benefits their overall development (brain, lung, eyes, skin, immune system, etc). However, initiation and advancement of enteral feedings in VLBW newborns is a challenge. Close to eighty percent of these babies will develop some type of feeding intolerance, presenting as any combination of the following: abdominal distension, abdominal tenderness, abdominal discoloration, visible bowel loops, abnormal stool patterns, bilious residuals or vomiting. A very small percentage of these babies will have necrotizing enterocolitis (NEC). The fear of NEC, which is associated with rapid advancement of feeds, contributes to slow advancement of feedings, leading to prolonged intravenous nutrition that offers complications, such as cholestasis, infection, and increased hospital stay and costs.

The ability to identify babies who can be safely fed from those who cannot will be a major breakthrough in neonatal medicine. Currently, decisions to feed these babies are based on subjective clinical indicators such as clinical appearance, measurement of gastric residuals and abdominal circumference. This leads to either aggressively feeding babies who are not yet ready and are at high risk for developing NEC, or to underfeeding babies who then develop growth failure, bowel atrophy, increased inflammatory responses, and sepsis. More objective measures of feeding tolerance are needed.

Currently used technologies to evaluate the gastrointestinal tract include radiography, ultrasound, nuclear scans, and manometry. All are suboptimal for the purpose of assessing feeding intolerance. For a baby to achieve enteral feedings safely, with minimal delays, feeding intolerance should be assessed accurately using bedside, non-invasive technology. Currently, no single method fulfills these criteria. However, it has been discovered that the simultaneous use of electrogastrography (EGG), electronic bowel sound/acoustic (AC) monitoring, and near-infrared spectroscopy (NIRS), have strong potential.

EGG measures gastrointestinal myoelectrical activities, non-invasively, using electrodes that are placed on the abdominal skin. EGG can provide information about a delay in gastric emptying associated with abnormal slow-wave patterns or post-prandial patterns. Because EGG is non-invasive and does not disturb ongoing physiologic activities, it is an attractive choice for studying infant gastrointestinal electrophysiology and motility. Bowel sounds are a result of vibration waves caused by contractions of the gut walls propelling intraluminal liquid and gas. Quantitative analysis of bowel sounds may help provide an objective interpretation of the acoustical activities of the intestine associated with motility. NIRS measures regional tissue oxygenation continuously at the bedside. Routine measurement of splanchnic circulation may identify infants at risk for disease and contribute to prevention. The combination of all three technologies would provide in-depth information on gut function that would assist clinicians in the initiation and advancement of enteral feedings.

EGG, AC, and NIRS, when used simultaneously, show promise as a clinical tool for the safe advancement of enteral feedings. Our purpose is to evaluate the simultaneous use of these three technologies to demonstrate feeding readiness patterns that can be readily applied to enhance enteral feeding and decrease morbidity in VLBW infants.

Methods

Participants

Thirty-three babies (23-32 week, mean 28 weeks, 17 female) in the neonatal intensive care unit at UF Health Shands Children's Hospital were enrolled in the study after parental permission. This study was approved by the Institutional Review Board at the University of Florida. Participants were premature newborns with birth weights less than 1500 grams, who were less than 4 weeks old and were receiving enteral tube feedings. Babies were excluded if they had any congenital or chromosomal disorders, major skin abnormalities, and faults in the skin integrity that preclude placement of skin sensors. Also excluded were newborns with questionable viability due to severe complications. Clinical outcomes were followed up until subjects were discharged.

Apparatus

EGG, AC, and NIRS were used simultaneously to detect patterns of gastrointestinal function.

Figure 7:
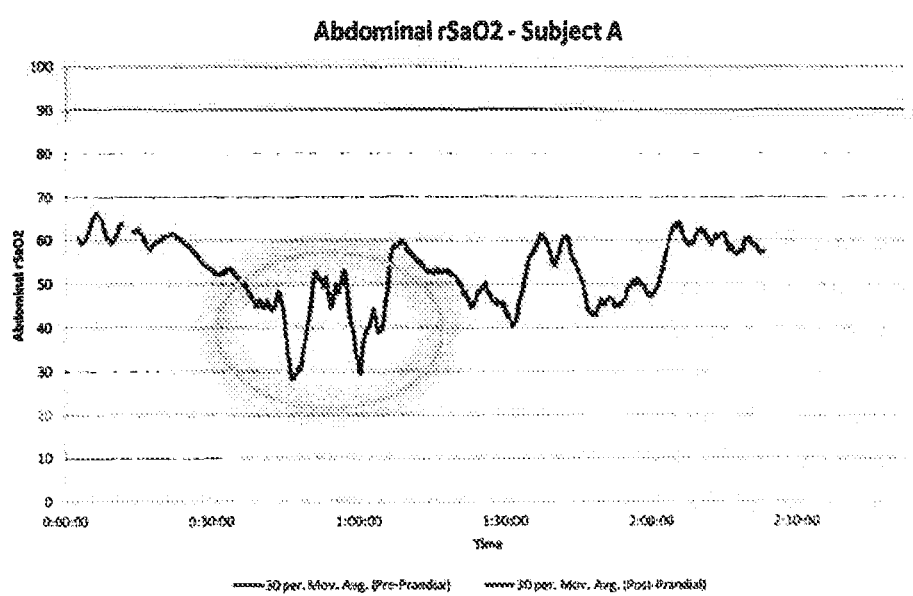
FIG. 7: NIRS showing post-prandial decrease in A-rSO2 for a participant born at 28 weeks gestation.

Electrogastrography (EGG):

3M Red Dot™ neonatal ECG electrodes were applied to the babies' abdominal skin as described and validated in Chen et al. 1999 and other studies.(2-6) Because of the small abdominal size of our patient population, we limited our setup to 3 electrodes (FIG. 7). The positive (black) electrode was placed midway between the umbilicus and xyphoid process. The negative (white) electrode was placed on the left upper quadrant, at the level of the mid-clavicular line, slightly above the level of the positive electrode. The ground (green) electrode was placed below the left costal margin, at the mid-axillary line, horizontal to the positive electrode, forming an equidistant triangle with the positive and negative electrodes. The electrodes were connected to the BIOPAC® MP36 System acquisition unit. The baby's legs were positioned 45 degrees with respect to the trunk.

Bowel Sound/Acoustic (AC) Monitoring

An electronic stethoscope (BIOPAC® SS17L microphone) was positioned to the left of the umbilicus and secured with 3M™ Double-Stick Disks. The electronic stethoscope was then connected to the BIOPAC® MP36 System acquisition unit.

Near-Infrared Spectroscopy (NIRS):

A neonatal OxyAlert® NIRSensor was placed to the right of the umbilicus and another on the baby's forehead. The sensors were connected to the INVOS System for processing. The cerebral sensor was used to check off irrelevant abdominal NIRS events and to calculate the cerebro-splanchnic oxygenation ratio (CSOR). (7, 8) The INVOS System and the participants' cardiorespiratory monitor were interfaced with the Vital Sync™ 5000 System for comparison on the same display and on the same time line.

Procedure

Because most babies in the NICU are on a 3-hour feeding schedule, measurements were obtained for 3 hours, i.e. 30-minute pre-prandial period and the entire post-prandial period that followed the enteral tube feeding. Recordings were repeated 3 times per infant as follows: 1) During the first week of starting enteral feeds at <50% of enteral goal feedings (10-40 mL/kg/day); 2) at 50-99% of goal feedings (41-129 mL/kg/day); and 3) at ≥100% of goal feedings (≥130 mL/kg/day). The initiation and advancement of enteral feedings were at the discretion of the on-service neonatologist.

No clinical decisions were made based on the results of the proposed technological measurement, because these have not been used previously for the purpose of evaluating enteral feeding capability. In this study, we were anticipating to measure gastric emptying responses induced by gastrointestinal myoelectrical and mechanoacoustic activities (via EGG and AC), and to measure oxygen balance in mesenteric tissues (via NIRS). If the research team were to notice an obvious finding that would be of benefit to the participant, the neonatologist would be informed. Data were collected and analyzed for feeding baselines, feeding advancements, and full feedings.

Data Processing

EGG: A Butterworth filter in a bandpass configuration was used to eliminate artifacts (only allowing 1 cpm to 16 cpm signals to pass). Because motion artifacts have a frequency greater than 16 cpm, these were filtered out. (9) Signal analyses were performed with Fast Fourier transformation (FFT) and spectral analysis to obtain measures of gastrointestinal function (EGG dominant frequency/power, percentage of normal gastric slow waves).(10, 11)

AC: An 80 Hz analog high-pass filter was used to suppress signals of cardiovascular origin. Measurements of sound amplitude, sound duration, number of sounds, and intervals between sounds were be obtained. Three-minute bins were used to calculate the sound index (SI) as the sum of absolute signal amplitutes (expressed in volts/minute) as described in previous bowel sound studies.(12, 13)

NIRS: Gross mean regional saturations were calculated for every subject's 3-hour testing period. Mean regional saturations were also calculated for each subject's pre-feeding and post feeding periods. The post-prandial period was divided into 10-minute intervals and each interval's mean regional saturation was compared with its respective pre-prandial mean regional saturation. Abdominal mean regional saturations were compared with cerebral mean regional saturations to check off irrelevant abdominal NIRS events and to calculate the cerebro-splanchnic oxygenation ratio (CSOR).(7, 8)

Statistical Analyses

Data were analyzed using an independent samples Mann-Whitney U Test to compare gastrointestinal function variables at each feeding milestone between the subject group <29 weeks gestation vs, the ≥29 weeks gestation group and to compare gastrointestinal function variables at each feeding milestone between the subject group that tolerated feeds vs, the subject group that developed feeding intolerance.

Results

Participants (n=33) were enrolled if they were born less than 34 weeks of gestation (mean 28 weeks) and less than or equal to 1500 grams (mean 1073.7 grams). 11 developed feeding intolerance during the course of their admission in the neonatal intensive care unit (Table 1). Of those who developed feeding intolerance, four had NEC.

TABLE 1

Participant Characteristics

|  | Total Subjects | Subjects w/ Feeding Intolerance | Subjects w/ Feeding Tolerance |
|---|---|---|---|
| N | 33 | 11 | 22 |
| Gender (F/M) | 19/14 | 5/6 | 14/8 |
| GA (wks) | | | |
| Mean ± SD (range) | 28 ± 2.4 (23-32 1/7) | 27 ± 3.1 (23-32 1/7) | 28.4 ± 2.1 (23 5/7-30 5/7) |
| GA distribution | | | |
| <29 wks GA | 16 | 8 | 8 |
| ≥29 wks GA | 17 | 3 | 14 |
| Birth weight (g) | | | |
| Mean ± SD (range) | 1073.7 ± 289.1 (545-1466) | 988.2 ± 315.3 (545-1392) | 1110.4 ± 277 (650-1466) |

Figure 8:
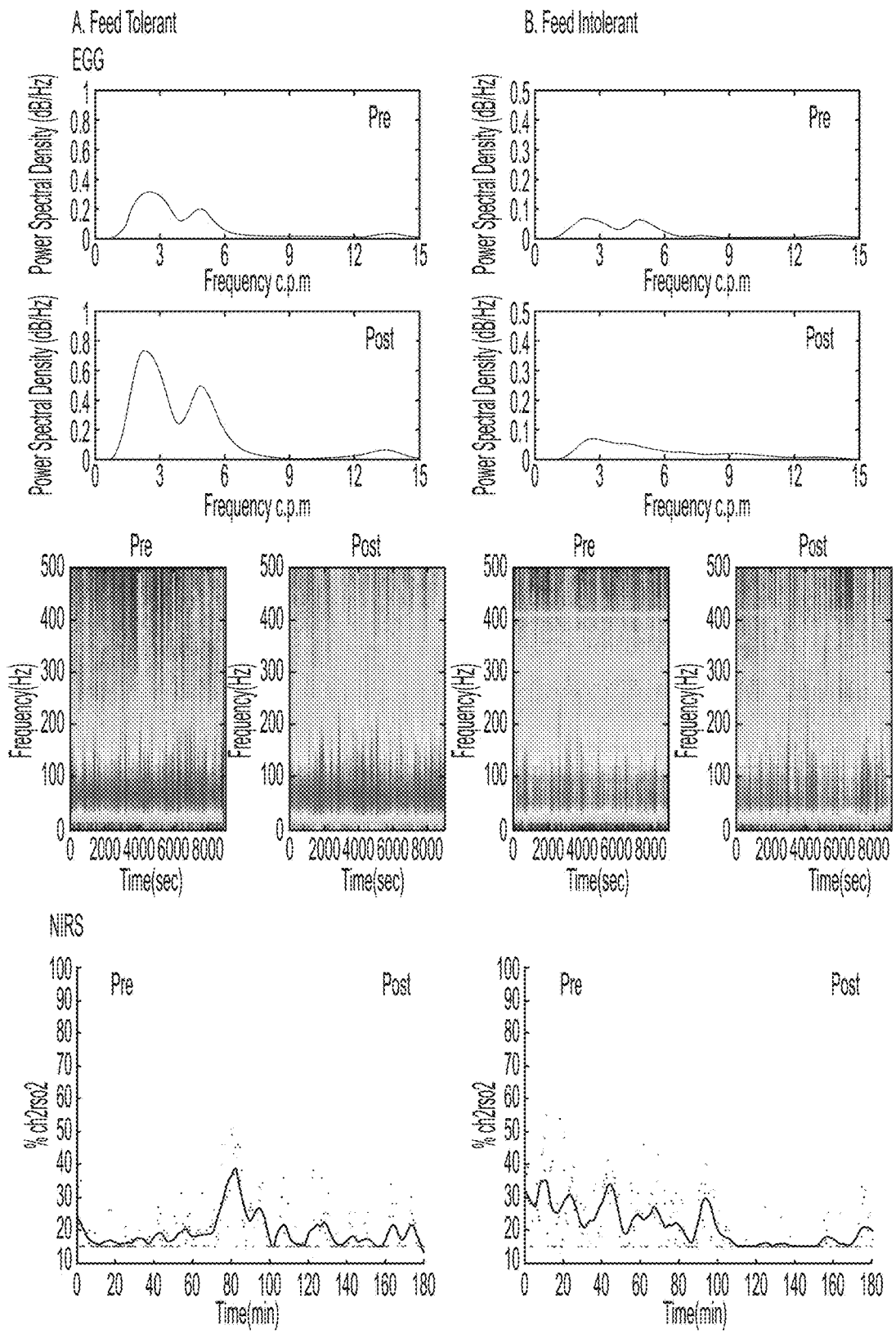
FIG. 8: Pre-prandial (Pre) and post-prandial (Post) EGG, AC, and NIRS results for A) a feeding-tolerant participant born at 26 4/7 weeks and weighing 905 grams. EGG power spectra results show a significant post-prandial increase in the power spectral density (amplitude) at the 3 cycle per minute (c.p.m) frequency of normal gastric slow wave. AC heat maps show an increase in the post-prandial amplitudes (warmer colors) for the feeding-tolerant baby. NIRS shows an increase in A-rSO2 at 60 minutes after feeding. B) A participant born at 26 weeks and weighing 1040 grams, who developed feeding intolerance 2-3 weeks after monitoring. EGG results prior to feeding intolerance show a lack of increase in the post-prandial power spectral density (amplitude) at the 3 cycle per minute (c.p.m) frequency of normal gastric slow wave. AC shows a lack of increase between pre- and post-prandial amplitudes. NIRS shows a decrease in A-rSO2 60 minutes after feeding.
Figure 9:
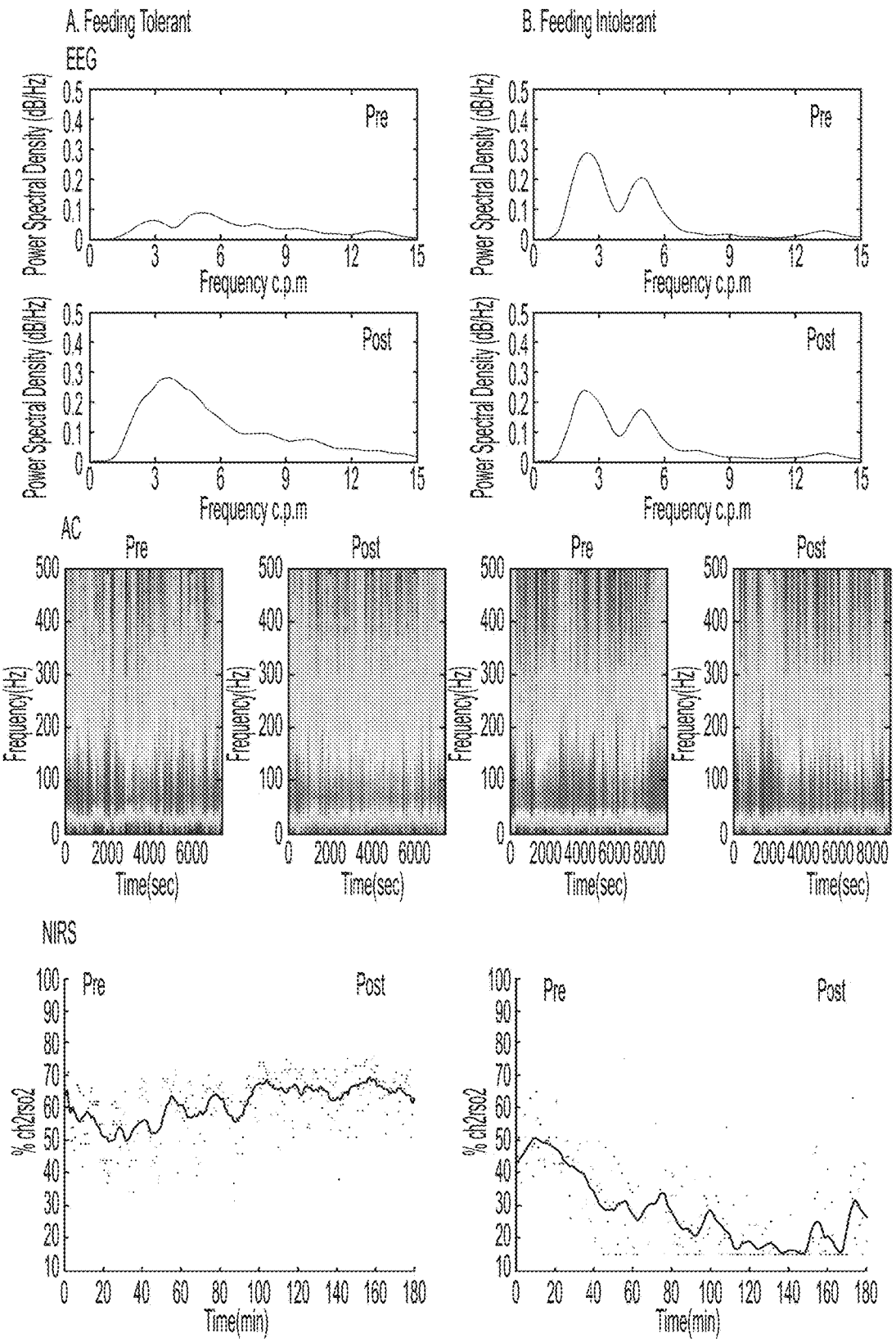
FIG. 9: A) Pre-prandial (Pre) and post-prandial (Post) EGG, AC, and NIRS results for A) a feeding-tolerant participant born at 30 5/7 weeks and weighing 1370 grams. EGG power spectra results show a significant post-prandial increase in the power spectral density (amplitude) at the 3 cycle per minute (c.p.m) frequency of normal gastric slow wave. AC heat maps show an increase in the post-prandial amplitudes (warmer colors) for the feeding-tolerant baby. NIRS shows an increase in A-rSO2 at 60 minutes after feeding. B) A participant born at 30 4/7 weeks and weighting 1393 grams, who developed feeding intolerance 2-3 weeks after monitoring. EGG results prior to feeding intolerance show a lack of increase in the post-prandial power spectral density (amplitude) at the 3 cycle per minute (c.p.m) frequency of normal gastric slow wave. AC shows a lack of increase between pre- and post-prandial amplitudes. NIRS shows a decrease in A-rSO2 60 minutes after feeding.

Babies who tolerated feeds had EGG and AC postprandial frequency spectra with significantly higher amplitudes than the pre-feeding frequency spectra (FIGS. 8A and 9A). Babies who developed feeding intolerance did not show this increase in amplitude (FIGS. 8B and 9B).

Figure 6:
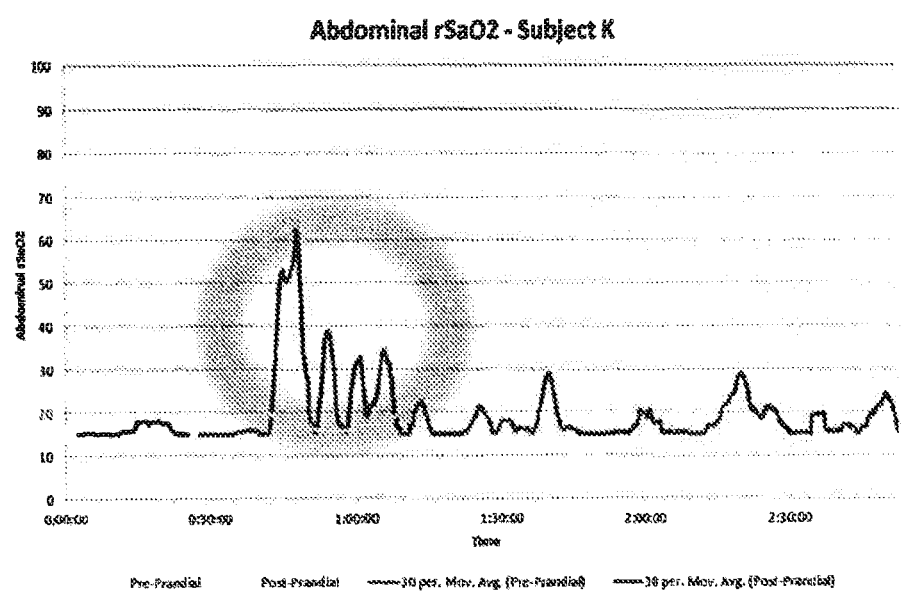
FIG. 6: NIRS showing a post-prandial increase in A-rSO2 for a participant born at 30 weeks Gestation.

Compared to their NIRS pre-prandial baseline, babies who showed a post-prandial increase in abdominal regional saturation (A-rSO2) did not develop feeding intolerance (FIG. 6). However, for 75% of babies less than 30 weeks and 50% of babies born after 30 weeks, results show a significant post-prandial decrease in A-rSO2 (FIG. 7). This decrease in A-rSO2 is seen approximately 60 minutes after a feeding event. Participants who developed feeding intolerance had the greatest decrease in A-rSO2 after feeding than other participants with matched corrected gestational ages.

Discussion

Currently used technologies to evaluate the gastrointestinal tract include radiography, ultrasound, nuclear scans and manometry. But all are suboptimal for the evaluation of feeding intolerance. Plain radiography is the standard of care to rule-out life-threatening conditions like NEC, bowel perforation, and bowel obstruction. However, it provides very limited information about gut motility and feeding readiness and provides only a snapshot of a single time point. Nuclear medicine studies can be used for motility evaluation; however, these are limited by poor image resolution, complex interpretation, practical difficulty of moving critically-ill patients to the testing site, and high levels of radiation exposure. Abdominal ultrasonography is able to detect intraabdominal fluid, bowel wall thickness, and bowel wall perfusion, providing information about gut motility and intestinal transit. However, ultrasonography requires state-of-the-art equipment and an experienced sonographer who masters the meticulous technique. Intraluminal manometry can be used to evaluate gut motility that can be useful in evaluating enteral feeding intolerance in preterm babies. However, its routine use is limited in premature babies because of its invasive nature. The simultaneous use of non-invasive technologies such as EGG, AC, and NIRS provides for the first time objective measures that will aid clinicians in the safe advancement of enteral feedings in VLBW neonates.

EGG measures gastrointestinal myoelectrical activities non-invasively using electrodes that are placed on the abdominal skin. Specifically, EGG can detect slow-wave activities of the stomach.(10) The cutaneous EGG slow-wave measurement is correlated with serosal EGG slow wave.(14) Single-channel EGGs can be used to measure gastric slow waves and relative contractile activities. However, to study the propagation of gastric slow waves and electrical coupling, a multichanned EGG is needed.(15)

In adults, EGG has been used to provide information about a delay in gastric emptying associated with abnormal slow-wave patterns or post-prandial patterns in diabetic gastroparesis, reflux disease, functional dyspepsia, and intestinal pseudo-obstruction. It has been determined that EGG is an attractive choice for studying infant gastrointestinal electrophysiology and motility Because EGG is noninvasive and does not disturb ongoing physiologic activities.

In newborns, EGG has been used to study the postnatal maturation effects on myoelectrical activities.(16-18) A normal response to feeding involves an increase in the amplitude of the gastric slow waves (at 2-4 c.p.m). (9, 11, 19, 20) Participants of the present study who were feeding-tolerant showed the same expected response. However, babies who eventually developed feeding intolerance showed an inability to increase the amplitude during the post-prandial period. Few studies have used EGG in the context of feeding intolerance. Zhang et al. showed that preterm infants had similar rhythmicity of gastric slow waves, but reduced amplitude compared to term infants. Although this may blame prematurity for the pattern seen with these babies it does not explain why it has been observed that they develop feeding intolerance. In addition, for these preterm infants in the study by Zhang et al, different methods of feeding (breastmilk vs. formula) showed minimal difference in the postprandial power at the dominant frequency of the EGG signal.(21) Riezzo and colleagues found that term babies who were breastfed had more adult-like fasting slow-wave activities than formula-fed term babies at 6 months of age.(22) In a different study, Riezzo and colleagues found no difference in myoelectrical activity in preterm infants who were fed hydrolysate vs. standard formula.(23) Other studies have used EGG to show that standard formulas supplemented with probiotics or probiotics may mimic breast milk from a functional standpoint, improving gastric motility in preterm babies.(24-26)

Bowel sounds are a result of vibration waves caused by contractions of the gut walls propelling intraluminal liquid and gas. Computerized bowel sound analysis is based on traditional abdominal auscultation, a component of routine physical examination. Qualitative characteristics of bowel sounds are bursts of GI acoustical activities, such as pops or clicks (associated with intestinal mixing) and rushes (associated with peristalsis). Quantitative analysis of bowel sounds may help provide an objective interpretation of the acoustical activities of the intestine associated with motility.

In adults, computerized bowel sound analysis has been used to investigate intestinal obstruction, acute abdomen, irritable bowel syndrome, small-volume ascites, and delayed gastric emptying. (27-31) However, very research has been conducted on computerized bowel sound analysis.

In the present study, when comparing the frequency spectra and power (amplitude) before and after feeding, babies who are feeding tolerant show an increase in both. This suggests an increase in bowel motility and peristalsis after feeding. In contrast babies who develop feeding intolerance do not show an increase in the frequency spectra and amplitude, suggesting a lack of normal increase in bowel motility and peristalsis after feeding. These AC results nicely match our EGG results indicating that the increase electrical activity seen by EGG can be associated with increased motility, as evidenced by AC.

Tomomasa and colleagues found that infants with pyloric stenosis had a gastrointestinal sound index that was significantly lower than that in healthy control infants. (32) The sound indices of the infants with pyloric stenosis began to increase 12 hours after surgery and reached the normal range by 48 hours. A relative scarcity of research exists in computerized bowel sound analysis even though it is non-invasive and a natural advancement of traditional bowel auscultation.

Near-infrared spectroscopy (NIRS) measures regional tissue oxygenation continuously at the bedside. In newborns, it has been used to evaluate cerebral circulation and the changes of cerebral oxyhemoglobin during treatment for respiratory distress and cardiac disease. NIRS monitoring equipment has also been applied to other body parts such as the flank and abdomen. Routine measurement of splanchnic circulation may identify infants at risk for disease and contribute to prevention.

In the first month of life, newborn infants may experience significant basal changes in intestinal vascular resistance. (33) An abdominal NIRS study of premature babies showed maturational changes of physiologic oxygen balance. For the first three postnatal weeks, there was an increase in the abdominal baseline of the regional oxygen saturation (from 32% to 66%) in stable preterm infants of (29-34) weeks gestation. (34)

In a study by Dave et al., NIRS was used to investigate the postprandial changes of mesenteric oxygenation due to feeding. (7) For the preterm infants between 32-35⁶⁄₇ weeks who were stable and tolerating orogastric feeds, A-rSO2 increased significantly 1 hour after feeding. In contrast, the present study showed that most of the participants did not show an increase, but a decrease in A-rSO2, 1-hour after feeding. This finding was seen more commonly in the most premature group of participants ≤29 weeks regardless of feeding tolerance outcomes. It is important to highlight that Dave et al. 2009 did not study subjects less than 32 weeks; therefore, the results may reflect a post-prandial "physiologic nadir" that may be specific to a more premature cohort. Of note, the present results show that participants who did show a post-prandial increase in A-rSO2, consistent with the results described in Dave et al. 2009, were feeding-tolerant. This finding may be predictive of a baby who may tolerate feeds whereas a decrease in post-prandial A-rSO2 may require additional evaluation with EGG and AC. Preliminary data indicates that lower EGG and AC signals after feeding indicate feeding intolerance. Conversely, higher signals after feeding is indicative of feeding tolerance.

Several studies have applied NIRS to abdominal investigation of bowel ischemia and NEC. Results from an observational cohort study of 40 neonates suggested that NIRS has potential value in the prediction of splanchnic ischemia. (8) A case study of a 4-week-old term infant with pulmonary atresia, intact ventricular septum, and multiple aortopulmonary collateral vessels reported the abdominal NIRS finding of significant mesenteric oxygen desaturation and associated NEC.(35)

Current NIRS devices are useful as trend monitors because of high inter-patient variability, causing difficulties in the definition of critical values of oxygen parameters. The main reason for this is the introduction of movement artifact and uncertain optical path length factor, especially in the abdominal measurements.

In conclusion, the simultaneous use of non-invasive technology such as EGG, AC, and NIRS demonstrate that they can be used as predictors of feeding tolerance. NIRS results that show an increase in A-rSO2 1 hour after feeding may be predictive that these babies will not develop feeding issues. However, a decrease in A-rSO2 requires additional evaluation by means of EGG and AC. For babies showing a decrease in A-rSO2 1 hour after feeding we are able to predict feeding tolerance if we also see an increase in post-prandial myoelectric amplitude at 3 c.p.m that is correlated with an increase in acoustic frequency and amplitude.

It should be borne in mind that all patents, patent applications, patent publications, technical publications, scientific publications, and other references referenced herein are hereby incorporated by reference in this application in order to more fully describe the state of the art to which the present invention pertains.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the preceding definitions are provided.

REFERENCES

1. Xu Y M, Zhu X P, Xiao Z, Yu L, Zhao X. Influence of aggressive nutritional support on growth and development of very low birth weight infants. Clin Exp Obstet Gynecol; 41:717-22.
2. Kasicka-Jonderko A, Jonderko K, Krusiec-Swidergol B, Obrok I, Blonska-Fajfrowska B. Comparison of multichannel electrogastrograms obtained with the use of three different electrode types. J Smooth Muscle Res 2006; 42:89-101.
3. Chen J D, Zou X, Lin X, Ouyang S, Liang J. Detection of gastric slow wave propagation from the cutaneous electrogastrogram. Am J Physiol 1999; 277:G424-30.
4. Rossi Z, Forlini G, Fenderico P, Cipolla R, Nasoni S. Electrogastrography. Eur Rev Med Pharmacol Sci 2005; 9:29-35.
5. Safder S, Chelimsky T C, O'Riordan M A, Chelimsky G. Gastric electrical activity becomes abnormal in the upright position in patients with postural tachycardia syndrome. J Pediatr Gastroenterol Nutr; 51:314-8.
6. Yin J, Chen J D. Electrogastrography: methodology, validation and applications. J Neurogastroenterol Motil 2013; 19:5-17.
7. Dave V, Brion L P, Campbell D E, Scheiner M, Raab C, Nafday S M. Splanchnic tissue oxygenation, but not brain tissue oxygenation, increases after feeds in stable preterm neonates tolerating full bolus orogastric feeding. J Perinatol 2009; 29:213-8.
8. Fortune P M, Wagstaff M, Petros A J. Cerebro-splanchnic oxygenation ratio (CSOR) using near infrared spectroscopy may be able to predict splanchnic ischaemia in neonates. Intensive Care Med 2001; 27:1401-7.
9. Chang F Y. Electrogastrography: basic knowledge, recording, processing and its clinical applications. J Gastroenterol Hepatol 2005; 20:502-16.
10. Chen J. A computerized data analysis system for electrogastrogram. 1992; 22:45.
11. Parkman H P, Hasler W L, Barnett J L, Eaker E Y. Electrogastrography: a document prepared by the gastric section of the American Motility Society Clinical GI Motility Testing Task Force. Neurogastroenterol Motil 2003; 15:89-102.

12. Tomomasa T, Morikawa A, Sandler R H, et al. Gastrointestinal sounds and migrating motor complex in fasted humans. Am J Gastroenterol 1999; 94:374-81.
13. Tomomasa T, Takahashi A, Nako Y, et al. Analysis of gastrointestinal sounds in infants with pyloric stenosis before and after pyloromyotomy. Pediatrics 1999; 104:e60.
14. Chen J D, Schirmer B D, McCallum R W. Serosal and cutaneous recordings of gastric myoelectrical activity in patients with gastroparesis. Am J Physiol 1994; 266:G90-8.
15. Lin X, Chen J Z. Abnormal gastric slow waves in patients with functional dyspepsia assessed by multichannel electrogastrography. 2001; 280:G1370.
16. Chen J D, Co E, Liang J, et al. Patterns of gastric myoelectrical activity in human subjects of different ages. Am J Physiol 1997; 272:G1022-7.
17. Liang J, Co E, Zhang M, Pineda J, Chen J D. Development of gastric slow waves in preterm infants measured by electrogastrography. Am J Physiol 1998; 274:G503-8.
18. Patterson M, Rintala R, Lloyd D A. A longitudinal study of electrogastrography in normal neonates. 2000; 35:59.
19. Devanarayana N M, de Silva D G, de Silva H J. Gastric myoelectrical and motor abnormalities in children and adolescents with functional recurrent abdominal pain. J Gastroenterol Hepatol 2008; 23:1672-7.
20. Lin Z, Chen J D, Schirmer B D, McCallum R W. Postprandial response of gastric slow waves: correlation of serosal recordings with the electrogastrogram. Dig Dis Sci 2000; 45:645-51.
21. Zhang J, Ouyang H, Zhu H B, et al. Development of gastric slow waves and effects of feeding in pre-term and full-term infants. 2006; 18:284.
22. Riezzo G, Castellana R M, de Bellis T, Laforgia F, Indrio F, Chiloiro M. Gastric electrical activity in normal neonates during the first year of life: effect of feeding with breast milk and formula. 2003; 38:836.
23. Riezzo G, Indrio F, Montagna O, et al. Gastric electrical activity and gastric emptying in preterm newborns fed standard and hydrolysate formulas. J Pediatr Gastroenterol Nutr 2001; 33:290-5.
24. Indrio F, Riezzo G, Raimondi F, Bisceglia M, Cavallo L, Francavilla R. The effects of probiotics on feeding tolerance, bowel habits, and gastrointestinal motility in pre-term newborns. 2008; 152:801.
25. Indrio F, Riezzo G, Raimondi F, Bisceglia M, Cavallo L, Francavilla R. Effects of probiotic and prebiotic on gastrointestinal motility in newborns. 2009; 60:27.
26. Indrio F, Riezzo G, Raimondi F, et al. Prebiotics improve gastric motility and gastric electrical activity in preterm newborns. J Pediatr Gastroenterol Nutr 2009; 49:258-61.
27. Yoshino H, Abe Y, Yoshino T, Ohsato K. Clinical application of spectral analysis of bowel sounds in intestinal obstruction. 1990; 33:753.
28. Sugrue M, Redfern M. Computerized phonoenterography: the clinical investigation of a new system. 1994; 18:139.
29. Craine B L, Silpa M, O'Toole C J. Computerized auscultation applied to irritable bowel syndrome. Dig Dis Sci 1999; 44:1887-92.
30. Liatsos C, Hadjileontiadis L J, Mavrogiannis C, Patch D, Panas S M, Burroughs A K. Bowel sounds analysis: a novel noninvasive method for diagnosis of small-volume ascites. Dig Dis Sci 2003; 48:1630-6.
31. Yamaguchi K, Yamaguchi T, Odaka T, Saisho H. Evaluation of gastrointestinal motility by computerized analysis of abdominal auscultation findings. J Gastroenterol Hepatol 2006; 21:510-4.
32. Tomomasa T, Morikawa A, Sandler R H, et al. Gastrointestinal sounds and migrating motor complex in fasted humans. 1999; 94:374.
33. Reber K M, Nankervis C A, Nowicki P T. Newborn intestinal circulation. Physiology and pathophysiology. 2002; 29:23.
34. McNeill S, Gatenby J C, McElroy S, Engelhardt B. Normal cerebral, renal and abdominal regional oxygen saturations using near-infrared spectroscopy in preterm infants. J Perinatol 2010; 31:51-7.
35. Stapleton G E, Eble B K, Dickerson H A, Andropoulos D B, Chang A C. Mesenteric oxygen desaturation in an infant with congenital heart disease and necrotizing enterocolitis. 2007; 34:442.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A method for diagnosing a digestion condition of a subject, the method comprising:
obtaining electrogastrogram (EGG), bowel sound, and Near Infrared Spectroscopy (NIRS) signals from an EGG sensor, acoustic sensor and NIRS sensor, respectively, positioned about an abdominal region of a subject;
removing artifacts from the signals to obtain conditioned signal data; and
determining a digestion condition of the subject based at least in part upon the conditioned signal data, wherein determining the digestion condition of the subject comprises identifying an abnormal digestion condition or the location or severity thereof.

2. The method of claim 1, further comprising determining gastrointestinal (GI) signal features from the conditioned GI signal data, wherein the digestion condition is based at least in part upon the GI signal features.

3. The method of claim 1, wherein the artifacts comprise movement artifacts, recording environment-related artifacts and sensor-related artifacts, or a combination thereof.

4. The method of claim 1, wherein the subject is a preterm infant.

5. The method of claim 4, wherein the infant is less than 34 weeks gestational, or less than 29 weeks gestational.

6. The method of claim 1, wherein the abnormal digestion condition is a post-prandial decrease of A-rSO2.

7. The method of claim 1, wherein the abnormal digestion condition is post-prandial decrease in EGG and/or AC signal levels.

8. The method of claim 1, further comprising:
determining with a processor a recording condition for each of the one or more sensors based upon predefined sensor criteria;
wherein when an acceptable recording condition is identified, one or more signals are obtained from the one or more sensors, and wherein when an unacceptable recording condition is identified, an indication of the sensor corresponding to the unacceptable recording condition is provided.

9. The method of claim 8, wherein following an indication of the sensor corresponding to the unacceptable recording condition, a communication to a user for correction of the unacceptable recording condition is provided.

10. The method of claim 8, further comprising amplification and filtering of the one or more obtained GI signals.

11. The method of claim 8, further comprising sampling the one or more obtained GI signals to obtain digital GI data.

12. A system for diagnosis of a digestion condition or feeding readiness of a subject, or a combination thereof, the system comprising:
 a signal recording module configured to acquire GI signals from one or more sensors positioned about an abdominal region of a subject, wherein the GI signals comprise electrogastrogram (EGG), bowel sound, and Near Infrared Spectroscopy (NIRS) signals from an EGG sensor, acoustic sensor and NIRS sensor, respectively;
 a signal conditioning module configured to condition GI signal data from the one or more GI signals, wherein the signal conditioning module is configured to remove artifacts associated with movement of the subject from the GI signal data;
 a signal analysis module configured to determine at least one feature of a GI signal based at least in part on the conditioned GI signal data; and
 a condition classification module configured to determine a digestion condition of the subject based at least in part on the at least one feature of the GI signal; wherein the signal conditioning module is configured to remove artifacts associated with movement of the subject from the GI signal data and the condition classification module is configured to identify a location and/or a severity of an abnormal digestion condition.

13. The system of claim 12, further comprising a sensor application module configured to verify a recording condition of the one or more sensors based upon predefined sensor criteria.

14. The system of claim 2, wherein the signal conditioning module is configured to remove artifacts associated with movement of the subject from the GI signal data.

15. The system of claim 12, wherein the at least one feature of the GI signal comprises a cerebrosplanchnic oxygen ratio value or a splanchnic circulation value, to determine if a subject is at risk for disease.

16. The system of claim 12, wherein a cerebrosplanchnic oxygen ratio is recorded by the signal recording module, and wherein the condition classification module determines a digestion condition of the subject based on the cerebrosplanchnic oxygen ratio.

17. The system of claim 16, wherein the digestion condition of the subject comprises an ability of the subject to tolerate an orogastric feed.

18. A system for diagnosis of a digestion condition and/or a feeding readiness of a subject and to identify a subject at risk for disease, comprising:
 a computer comprising a computer processing module or modules to process (i) an EGG signal input; (ii) a bowel sound input and (iii) a NIRS input;
 a display to present data to an operator of the system; and
 an EGG probe, a bowel sound stethoscope and an NIRS probe in communication with said computer; and determining with the computer a digestion condition of the subject based at least in part upon the EGG, bowel sound and NIRS input data, wherein determining the digestion condition of the subject comprises identifying an abnormal digestion condition or the location or severity thereof.

19. The system of claim 18, further comprising a signal conditioning module configured to condition one or more of (i), (ii) or (iii) inputs.

* * * * *